US011219759B2

(12) United States Patent
Leven et al.

(10) Patent No.: US 11,219,759 B2
(45) Date of Patent: Jan. 11, 2022

(54) SYSTEMS AND METHODS FOR INTRODUCING AN ELECTRICAL STIMULATION LEAD INTO A PATIENT

(71) Applicant: Boston Scientific Neuromodulation Corporation, Valencia, CA (US)

(72) Inventors: Jacob B. Leven, Huntington Beach, CA (US); Kevin Peng Wang, Fremont, CA (US); Rhys Wheatley, Sonoma, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 580 days.

(21) Appl. No.: 16/113,210

(22) Filed: Aug. 27, 2018

(65) Prior Publication Data
US 2019/0060643 A1 Feb. 28, 2019

Related U.S. Application Data

(60) Provisional application No. 62/551,628, filed on Aug. 29, 2017, provisional application No. 62/585,419, filed on Nov. 13, 2017.

(51) Int. Cl.
*A61N 1/05* (2006.01)
*A61N 1/36* (2006.01)
*A61B 17/32* (2006.01)

(52) U.S. Cl.
CPC .............. *A61N 1/0558* (2013.01); *A61B 2017/320056* (2013.01); *A61N 1/36075* (2013.01)

(58) Field of Classification Search
CPC .............. A61N 1/0558; A61N 1/36075; A61B 2017/320056
See application file for complete search history.

(56) References Cited

U.S. PATENT DOCUMENTS

| 4,285,347 A | 8/1981 | Hess |
| 5,193,539 A | 3/1993 | Schulman et al. |
| 5,193,540 A | 3/1993 | Schulman et al. |
| 5,312,439 A | 5/1994 | Loeb |
| 5,324,316 A | 6/1994 | Schulman et al. |
| 5,376,108 A * | 12/1994 | Collins .................. A61N 1/056 604/174 |

(Continued)

OTHER PUBLICATIONS

U.S. Appl. No. 62/621,837, filed Jan. 25, 2018.

*Primary Examiner* — Amanda K Hulbert
*Assistant Examiner* — Natasha Patel
(74) *Attorney, Agent, or Firm* — Branch Partners PLLC; Bruce E. Black

(57) ABSTRACT

A medical device kit includes a tunneling tool configured to form a tunnel through patient tissue for receiving an electrical stimulation lead. The tunneling tool includes a tunneling-tool body having an elongated shape with a proximal portion and a distal portion. The tunneling-tool body is formed from a material configured to be manually bent prior to insertion into patient tissue to conform to an anatomical contour through which the tunnel is to extend. A blunt tip is disposed at the distal portion. The blunt tip is configured to tunnel through patient tissue. A tunneling-tool suture-receiving element is disposed along the proximal portion of the tunneling-tool body. The tunneling-tool suture-receiving element is configured to receive a suture extendable along the tunnel formed by the tunneling tool.

19 Claims, 12 Drawing Sheets

(56) References Cited

U.S. PATENT DOCUMENTS

| | | |
|---|---|---|
| 5,405,367 A | 4/1995 | Schulman et al. |
| 5,902,320 A * | 5/1999 | Matsutani .......... A61B 17/0625 606/222 |
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,392,093 B2 | 6/2008 | Khan |
| 7,450,997 B1 | 11/2008 | Pianca et al. |
| 7,519,433 B2 | 4/2009 | Foley |
| 7,660,631 B2 | 2/2010 | Whitehurst et al. |
| 7,672,734 B2 | 3/2010 | Anderson et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,949,395 B2 | 5/2011 | Kuzma |
| 7,974,706 B2 | 7/2011 | Moffitt et al. |
| 8,175,710 B2 | 5/2012 | He |
| 8,214,048 B1 | 7/2012 | Whitehurst et al. |
| 8,224,450 B2 | 7/2012 | Brase |
| 8,271,094 B1 | 9/2012 | Moffitt et al. |
| 8,295,944 B2 | 10/2012 | Howard et al. |
| 8,364,278 B2 | 1/2013 | Pianca et al. |
| 8,391,985 B2 | 3/2013 | McDonald |
| 8,688,235 B1 | 4/2014 | Pianca et al. |
| 9,283,394 B2 | 3/2016 | Whitehurst et al. |
| 2002/0143376 A1 * | 10/2002 | Chinn .................... A61N 1/05 607/115 |
| 2006/0036286 A1 | 2/2006 | Whitehurst et al. |
| 2007/0150036 A1 | 6/2007 | Anderson |
| 2009/0187222 A1 | 7/2009 | Barker |
| 2009/0276021 A1 | 11/2009 | Meadows et al. |
| 2010/0076535 A1 | 3/2010 | Pianca et al. |
| 2010/0268298 A1 | 10/2010 | Moffitt et al. |
| 2011/0004267 A1 | 1/2011 | Meadows |
| 2011/0005069 A1 | 1/2011 | Pianca |
| 2011/0071540 A1 | 3/2011 | Kast et al. |
| 2011/0078900 A1 | 4/2011 | Pianca et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0316615 A1 | 12/2012 | DiGiore et al. |
| 2013/0105071 A1 | 5/2013 | DiGiore et al. |
| 2013/0197602 A1 | 8/2013 | Pianca et al. |
| 2014/0276928 A1 * | 9/2014 | Vanderpool .......... A61B 17/3468 606/129 |
| 2015/0258313 A1 * | 9/2015 | Seaver .............. A61M 25/0194 604/8 |
| 2015/0343197 A1 | 12/2015 | Gardeski et al. |
| 2016/0166828 A1 * | 6/2016 | Yu ........................ A61N 1/0558 607/116 |

* cited by examiner

SYSTEMS AND METHODS FOR INTRODUCING AN ELECTRICAL STIMULATION LEAD INTO A PATIENT

CROSS-REFERENCE TO RELATED APPLICATIONS

This application claims the benefit under 35 U.S.C. § 119(e) of U.S. Provisional Patent Application Ser. No. 62/585,419, filed Nov. 13, 2017, and U.S. Provisional Patent Application Ser. No. 62/551,628, filed Aug. 29, 2017, both of which are incorporated herein by reference.

FIELD

The present invention is directed to the area of implantable electrical stimulation systems and methods of making and using the systems, and in particular, to systems and devices for introducing electrical stimulation leads into a patient, as well as methods of making and using the systems and devices for introducing the electrical stimulation leads.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator) and one or more stimulator electrodes. The one or more stimulator electrodes can be disposed along one or more leads, or along the control module, or both. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a medical device kit that includes a tunneling tool configured to form a tunnel through patient tissue for receiving an electrical stimulation lead. The tunneling tool includes a tunneling-tool body having an elongated shape with a proximal portion and a distal portion. The tunneling-tool body is formed from a material configured to be manually bent prior to insertion into patient tissue to conform to an anatomical contour through which the tunnel is to extend. A blunt tip is disposed at the distal portion. The blunt tip is configured to tunnel through patient tissue. A tunneling-tool suture-receiving element is disposed along the proximal portion of the tunneling-tool body. The tunneling-tool suture-receiving element is configured to receive a suture extendable along the tunnel formed by the tunneling tool.

In at least some embodiments, the blunt tip of the tunneling tool is not sufficient to pierce patient skin. In at least some embodiments, the tunneling tool is formed from annealed steel. In at least some embodiments, the medical device kit further includes at least one suture attached to the tunneling-tool suture-receiving element.

In at least some embodiments, the medical device kit further includes a lead blank configured to expand a tunnel formed by the tunneling tool along at least one lateral dimension when the lead blank is extended through the tunnel, the lead blank having at least one lateral dimension that is larger than any lateral dimension of the tunneling tool. In at least some embodiments, the lead blank includes at least one lead-blank suture-receiving element configured for receiving the suture extended through the tunnel by the tunneling tool and being pulled through the tunnel using the suture. In at least some embodiments, the lead blank is a single-piece structure. In at least some embodiments, the lead blank is a multi-piece structure that includes a first piece and at least one longitudinally-offset second piece coupled, or coupleable, to the first piece, where the first piece and the at least one second piece are each configured to expand patient tissue. In at least some embodiments, a largest lateral dimension of the first piece is smaller than a largest lateral dimension of the at least one second piece.

In another embodiment, a medical device system includes any of the medical device kits described above and an electrical stimulation lead configured for insertion into a tunnel formed by the tunneling tool of the medical device kit. The electrical stimulation lead includes a lead body having a proximal portion and a distal portion; electrodes disposed along the distal portion of the lead body; and a lead suture-receiving element coupled, or coupleable, to the lead body. The lead suture-receiving element is configured to receive a suture extending through the tunnel formed by the tunneling tool and being pulled through the tunnel using the suture.

In at least some embodiments, the tunneling-tool body has a largest lateral dimension that is no larger than a largest lateral dimension of the lead body. In at least some embodiments, at least one of the tunneling-tool suture-receiving element or the lead suture-receiving element is formed as an eyelet. In at least some embodiments, the lead suture-receiving element is disposed along the distal portion of the lead body. In at least some embodiments, the lead suture-receiving element is disposed along the proximal portion of the lead body.

In at least some embodiments, the medical device system further includes a lead blank configured to expand a tunnel formed by the tunneling tool prior to insertion of the electrical stimulation lead into the tunnel, the lead blank including a first lead blank suture-receiving element and a second lead blank suture-receiving element, the first lead blank suture-receiving element configured to couple to the tunneling-tool suture-receiving element of the tunneling tool by a first suture, and the second lead blank suture-receiving element configured to couple to the lead suture-receiving element by a second suture.

In yet another embodiment, an implantable electrical stimulation lead includes a lead body having a distal portion and an opposing proximal portion; electrodes disposed along the distal portion of the lead body; terminals disposed along the proximal portion of the lead body; and conductors electrically coupling the terminals to the electrodes. A suture-receiving element is configured to receive a suture disposed along patient tissue. The suture-receiving element includes either a) at least one of an eyelet disposed along a plug coupleable with the distal tip of the lead body or b) elongated material partially disposed in the lead body and forming a loop extending outwardly from the distal tip.

In still yet another embodiment, a method for implanting an electrical stimulation lead into a patient includes providing any of the medical device systems described above. A suture is extended through a tunnel formed through patient tissue, using the tunneling tool of the medical device system, from an entry location where the tunnel enters patient tissue to an egress location distinct from the entry location where the tunnel exits patient tissue. The electrical stimulation lead of the medical device system is pulled into the tunnel using the suture.

In at least some embodiments, extending the suture through the tunnel includes exiting patient tissue at an intermediate waypoint along the tunnel between the entry location and the egress location and re-entering patient tissue at the intermediate waypoint.

In at least some embodiments, pulling the electrical stimulation lead of the medical device system into the tunnel using the suture includes pulling the distal portion of the electrical stimulation lead to a location within the tunnel that is in proximity to a target stimulation location.

In at least some embodiments, the method further includes enlarging at least a portion of the tunnel along at least one lateral dimension by pulling a lead blank through at least a portion of the tunnel from either the entry location or the egress location using the suture, and using the lead blank for pulling the electrical stimulation lead of the medical device system into the tunnel using another suture. In at least some embodiments, pulling the lead blank through at least a portion of the tunnel includes pulling the lead blank along less than half of a length of the tunnel in a first direction, and subsequently pulling the lead blank in a second direction that is opposite to the first direct to remove the lead blank from the tunnel, thereby forming a pocket along one end of the tunnel with at least one lateral dimension that is larger than any lateral dimension of the remaining portions of the tunnel.

In another embodiment, a method of anchoring an electrical stimulation lead to patient tissue includes providing any of the implantable electrical stimulation leads described above. The implantable electrical stimulation lead is advanced to a target location within a patient. The suture-receiving element of the electrical stimulation lead is attached to patient tissue, via the suture, to anchor the electrical stimulation lead in proximity to the target location.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
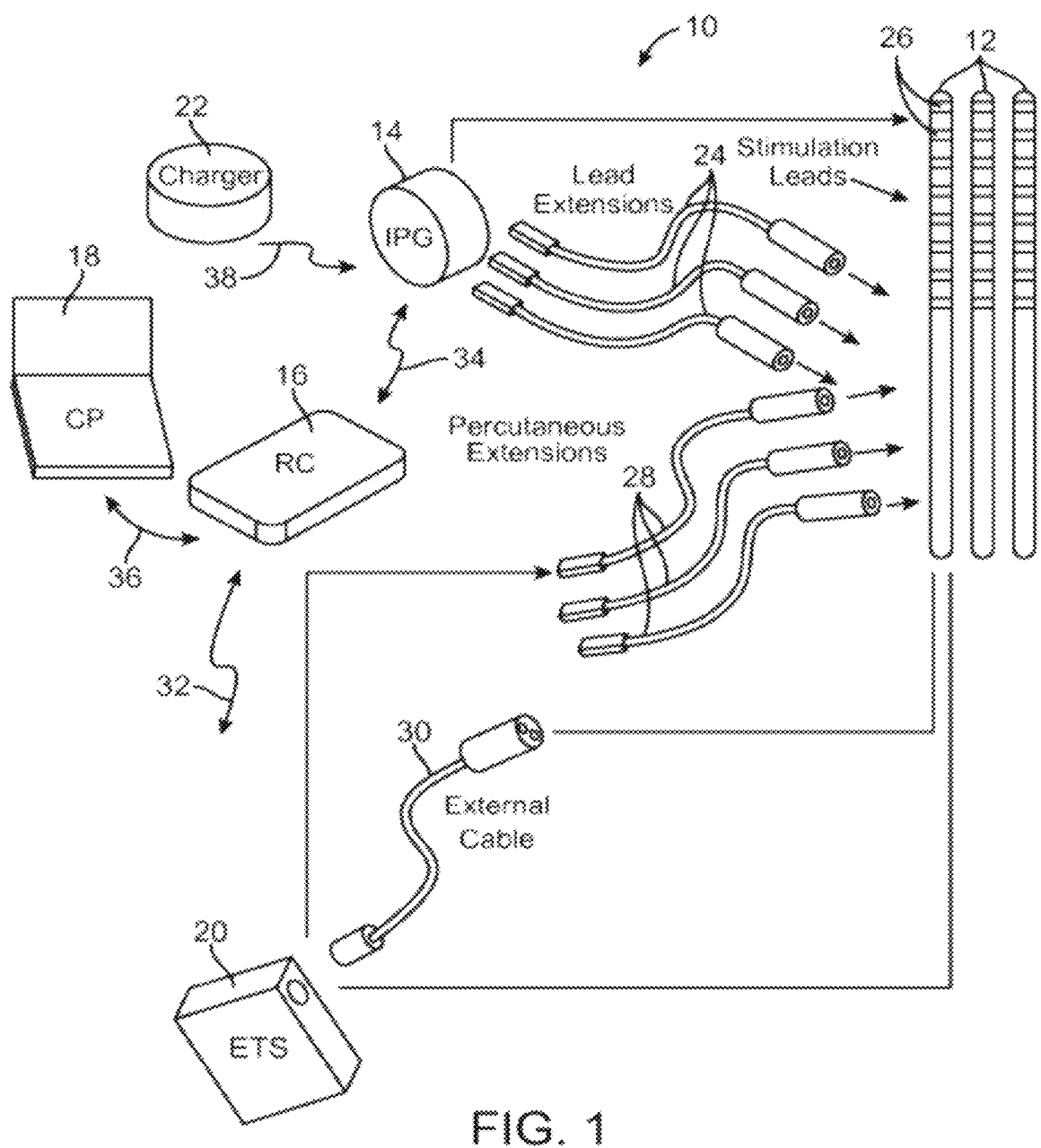
FIG. 1 is a schematic view of one embodiment of an electrical stimulation system, according to the invention.

The present invention is directed to the area of implantable electrical stimulation systems and methods of making and using the systems, and in particular, to systems and devices for introducing electrical stimulation leads into a patient, as well as methods of making and using the systems and devices for introducing the electrical stimulation leads.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference.

Suitable implantable electrical stimulation systems may also include one or more microstimulators, which include an implantable control module containing electrical circuitry connected to one or more electrodes that extend through, or along, one or more walls of the control module. In some instances, microstimulators include segmented electrodes. Examples of microstimulators are found in, for example, U.S. Pat. Nos. 5,193,539; 5,193,540; 5,312,439; 5,324,316; 5,405,367; 7,660,631; 8,214,048; 9,283,394; and U.S. Patent Applications Publication No. 2006/0036286, all of which are incorporated by reference.

In the discussion below, a percutaneous lead will be exemplified, but it will be understood that the methods and systems described herein are also applicable to paddle leads and other leads, as well as to microstimulators.

A percutaneous lead for electrical stimulation (for example, deep brain, spinal cord, peripheral nerve, or cardiac-tissue stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. For illustrative purposes, the leads are described herein relative to use for deep brain stimulation, but it will be understood that any of the leads can be used for applications other than deep brain stimulation, including spinal cord stimulation, peripheral nerve stimulation, dorsal root ganglion stimulation, sacral nerve stimulation, or stimulation of other nerves, muscles, and tissues.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity. The implantable pulse generator can have eight stimulation channels which may be independently programmable to control the magnitude of the current stimulus from each channel. In some embodiments, the implantable pulse generator can have more or fewer than eight stimulation channels (e.g., 4-, 6-, 16-, 32-, or more stimulation channels). The implantable pulse generator can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Turning to FIG. 2, electrical stimulation leads are currently implanted in many different locations throughout a patient's body. Implantation of electrical stimulation leads into some body locations suitable for receiving stimulation may be unduly challenging. For example, in the case of peripheral nerve stimulation or peripheral nerve field stimulation, a lead may be implanted along a patient's face. The human face includes multifaceted geometries with only a thin layer of tissue separating skin from bone. Additionally, the human face is a bodily region where it is desired to reduce as much potential cosmetic damage caused by a lead implantation procedure as possible.

One conventional method of implanting an electrical stimulation lead includes using a hypodermic needle to tunnel under a patient's skin, and then place the lead through the needle. In order to fit the lead in the needle, the needle typically has a larger diameter than the lead. This may be undesired when introducing the lead into a confined space, such as along the patient's face, where reducing potential cosmetic damage caused by a lead implantation procedure can be especially important. Additionally, hypodermic needles are typically formed from hardened steel and are not designed for bending. Thus, when implanting a lead into a bodily region with multifaceted geometries and only a thin layer of tissue separating skin and bone, the needle may not be able to adapt to anatomical contours.

As herein described, a tunneling tool can be used to form a tunnel suitable for receiving an electrical stimulation lead. The tunneling tool is adapted to include a suture-receiving element to which one or more sutures can be attached. The tunneling tool can be extended through the tunnel, leaving the suture(s) behind. The suture(s) can then be used to pull the electrical stimulation lead through at least a portion of the tunnel to a desired location, such as a target stimulation location. In at least some embodiments, one or more optional lead blanks are used to expand the tunnel along at least one lateral dimension after the tunneling tool forms the tunnel and before the lead is pulled into the tunnel.

Figure 2A:
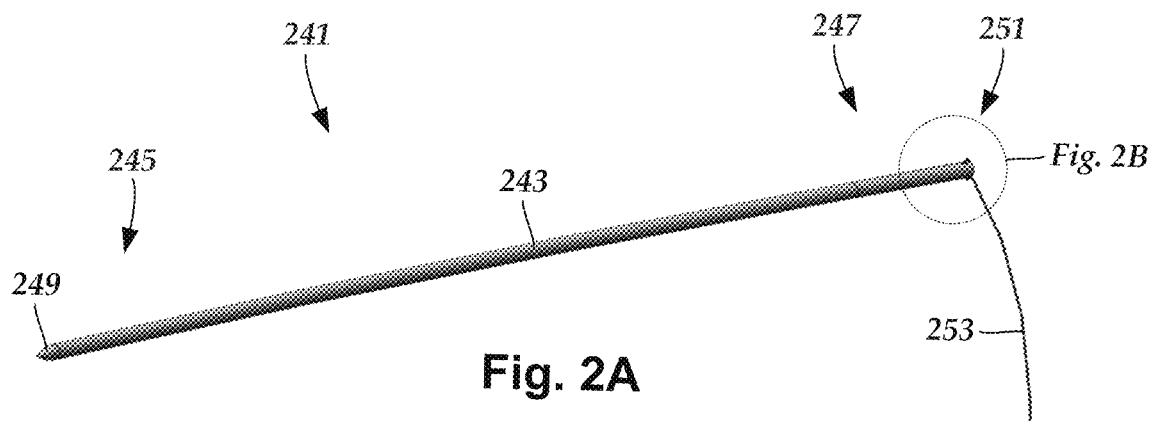
FIG. 2A is a schematic perspective view of one embodiment of a tunneling tool with a blunt distal tip and a suture-receiving element at a proximal end, according to the invention.

FIG. 2A shows, in perspective view, one embodiment of a tunneling tool 241 suitable for tunneling through patient tissue. The tunneling tool 241 includes a body 243 having an elongated shape with a distal end 245 and a proximal end 247. The distal end 245 of the body 243 includes a blunt tip 249 suitable for advancing the tunneling tool 241 through patient tissue. The proximal end 247 of the body 243 includes a tunneling-tool suture-receiving element 251 suitable for receiving one or more sutures 253.

The one or more sutures can be any suitable elongated material (e.g., thread, cable, fiber, cord, strand, wire, or the like) suitable for extending through a tunnel formed in patient tissue, and being used to pull an electrical stimulation lead along at least a portion of the tunnel. The one or more sutures can be single filament (or strand), or multi-filar (or multi-stranded), or a combination of both. When multiple sutures are utilized, the sutures may each extend the entire length of the tunnel, or at least some of the multiple sutures can be connected together end-to-end. For convenience, the term "suture" will be used herein, and is intended to cover either a single suture or multiple sutures.

The body 243 is formed from any suitable biocompatible material having sufficient column strength to tunnel through patient tissue. In at least some embodiments, the body 243 is formed from annealed steel. Other suitable materials can be used in lieu of, or in addition to, annealed steel including, for example, spring steel or surgical steel. In at least some embodiments, the body 243 is bendable to enable a medical practitioner to adjust the shape of the body 243 to conform to an anatomical contour along which a tunnel is to extend.

The body 243 can have any lateral profile suitable for forming a tunnel sufficient to receive a lead. Note that a lateral dimension is a dimension perpendicular to a longitudinal length. Note also, that "lateral" and "transverse" are used interchangeably herein. In at least some embodiments, the tunneling tool 241 has an isodiametric lateral profile along the entire longitudinal length of the body 243 proximal from the blunt tip 249. In at least some embodiments, the tunneling tool 241 has an isodiametric lateral profile along the entire longitudinal length of the body 243 proximal from the blunt tip 249 and distal to the tunneling-tool suture-receiving element 251.

Figure 2B:
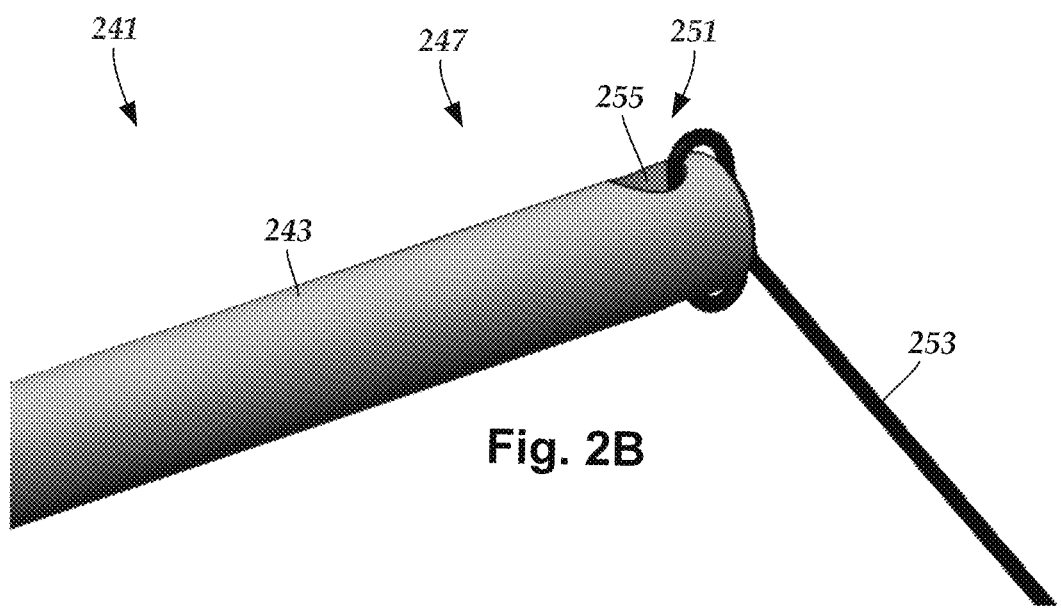
FIG. 2B is a schematic close-up perspective view of one embodiment of the suture-receiving element of FIG. 2A, according to the invention.

FIG. 2B shows, in schematic close-up perspective view, one embodiment of the tunneling-tool suture-receiving element 251. In at least some embodiments, the tunneling-tool suture-receiving element 251 defines an eyelet 255 through which the suture 253 can be extended. In some embodiments, the suture 253 is pretied to the suture-receiving element 251. In other embodiments, the suture 253 is manually tied to the suture-receiving element 251 prior to forming a tunnel using the tunneling tool 241.

Figure 3:
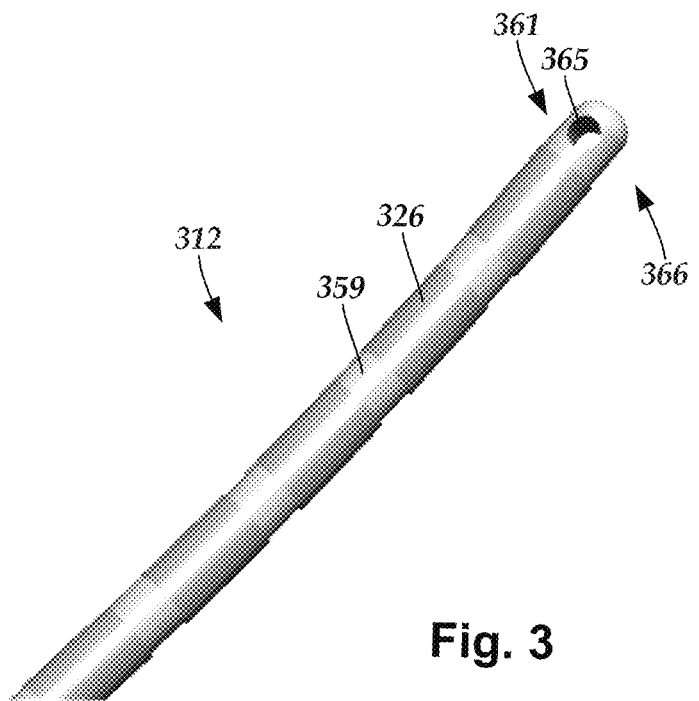
FIG. 3 is a schematic perspective view of one embodiment of a portion of an electrical stimulation lead with a first embodiment of a suture-receiving element disposed along a distal portion of the lead, according to the invention.

Turning to FIG. 3, a suture-receiving element can be disposed along an electrical stimulation lead. In at least some embodiments, a lead suture-receiving element is used to pull the lead along a tunnel by attaching the lead suture-receiving element to a suture extending along the tunnel and using the suture to pull the lead. In at least some embodiments, the lead suture-receiving element is used to anchor an electrical stimulation lead to patient tissue (e.g., fascia) to reduce, or even prevent, lead migration. For example, a suture can be attached to the lead suture-receiving element and used to tie the lead to patient tissue at a target stimulation location. In at least some embodiments, the lead suture-receiving element is used to pull the lead along a tunnel, and also to anchor the lead to patient tissue.

FIGS. 3-4B and 14-16 show the lead suture-receiving elements disposed along the distal portions of leads only, for clarity of illustration. The lead suture-receiving elements shown in FIGS. 3-4B and 14-16 are equally applicable for being disposed along the proximal portions of leads in addition to, or in lieu of, disposing the lead suture-receiving elements along the distal portions of leads, as leads can be pulled along a tunnel and/or anchored to patient tissue from either end of the lead. Additionally, the lead suture-receiving elements shown in FIGS. 3-4B and 14-16 are equally applicable for being disposed along a tunneling tool or a lead blank in addition to, or in lieu of, along either end of an electrical stimulation lead.

FIG. 3 shows, in schematic perspective view, one embodiment of a distal portion of an electrical stimulation lead 312 that includes a body 359 and electrodes, such as electrode 326, disposed along the body 359. A lead suture-receiving element 361 is disposed along the lead 312 and is configured to receive a suture. In at least some embodiments, the lead suture-receiving element 361 defines an eyelet 365 through which a suture (e.g., suture 253 of FIGS. 2A-2B) can be extended. In FIG. 3, the eyelet 365 is shown extending through the body 359 at a distal tip 366 of the lead. In at least some embodiments, the eyelet 365 extends through the body 359 at a location proximal to the distal tip 366. In at least some embodiments, the eyelet 365 extends through the body 359 at a location between two or more electrodes 326. In at least some embodiments, the eyelet 365 extends through at least one of the electrodes 326.

Figure 4A:
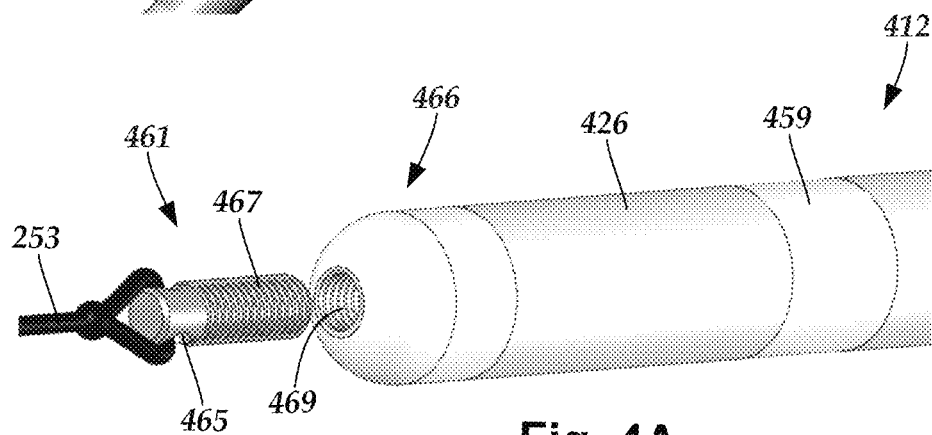
FIG. 4A is a schematic perspective view of one embodiment of a portion of an electrical stimulation lead with a second embodiment of a suture-receiving element disposed along a distal portion of the lead, according to the invention.
Figure 4B:
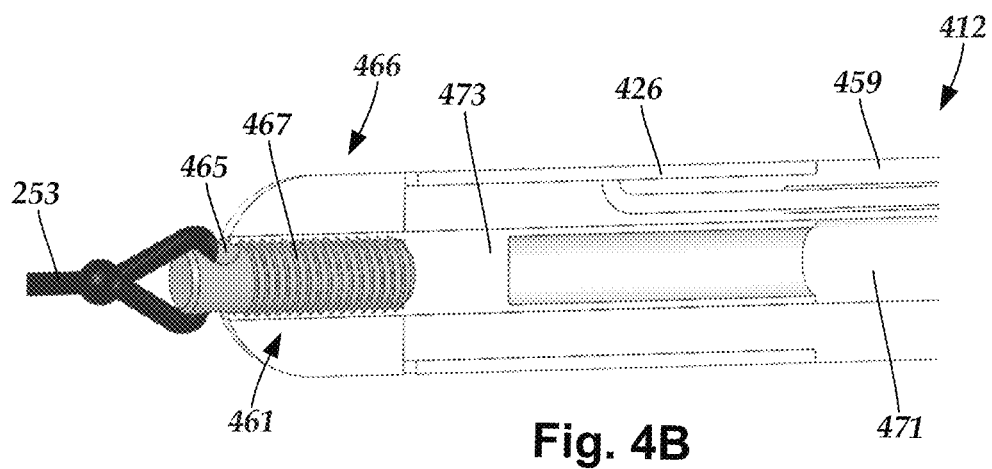
FIG. 4B is a schematic perspective view of one embodiment of the electrical stimulation lead of FIG. 4A shown in longitudinal cross-section, according to the invention.

In at least some embodiments, the lead suture-receiving element is formed as a plug coupleable with the lead. FIG. 4A shows, in schematic perspective view, one embodiment of a portion of an electrical stimulation lead 412 and a plug 467 suitable for coupling to the lead 412. FIG. 4B shows a perspective view of the lead 412 in longitudinal cross-section with the plug 467 coupled to the lead 412. The lead 412 includes a body 459 and electrodes, such as electrode 426, disposed along the body 459. A lead suture-receiving element 461 is disposed along the plug 467 and is configured to receive the suture 253.

In at least some embodiments, the lead suture-receiving element 461 defines an eyelet 465 configured to receive the suture 253. In some embodiments, the suture 253 is pre-attached to the plug 467 prior to distribution to an end user. In other embodiments, the suture 253 is tied to the plug 467 by a medical practitioner. In at least some embodiments, the plug 467 is insertable into a plug-receiving aperture 469 defined along a distal tip 466 of the lead 412. The plug 467 can couple with the plug-receiving aperture 469 in any suitable manner. In the illustrated embodiment, the plug 467 includes threads that mate with complementary threads along walls of the plug-receiving aperture 469.

In at least some embodiments, the lead includes at least one central lumen 471, such as a stylet lumen for receiving a stylet, for facilitating placement of the lead within a patient. In at least some embodiments, the lead 412 includes an end-stop 473 providing a barrier between the central lumen 471 and the plug-receiving aperture 469 to prevent a stylet from undesirably extending out of the lead through the plug-receiving aperture 469 when the plug 469 is not disposed in the plug-receiving aperture 469, and also preventing undesirable over-insertion of the plug 469 into the plug-receiving aperture 469.

Figure 14:
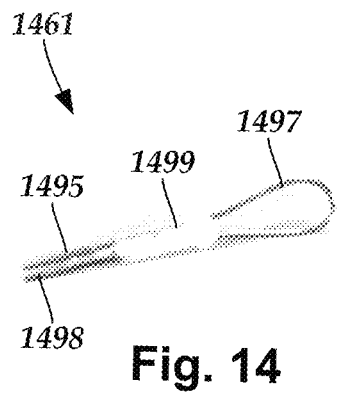
FIG. 14 is a schematic side view of a third embodiment of a suture-receiving element, the suture-receiving element including a wire bent into a loop suitable for receiving a suture, according to the invention.
Figure 15:
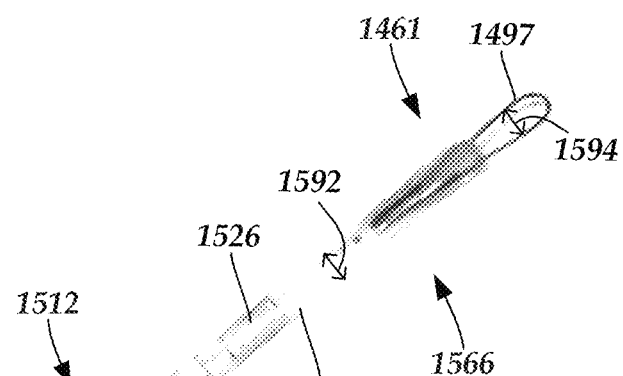
FIG. 15 is a schematic perspective view of one embodiment of the suture-receiving element of FIG. 14 partially disposed within a body of an electrical stimulation lead with the wire loop of the suture-receiving element extending outwardly from the lead, according to the invention.
Figure 16:
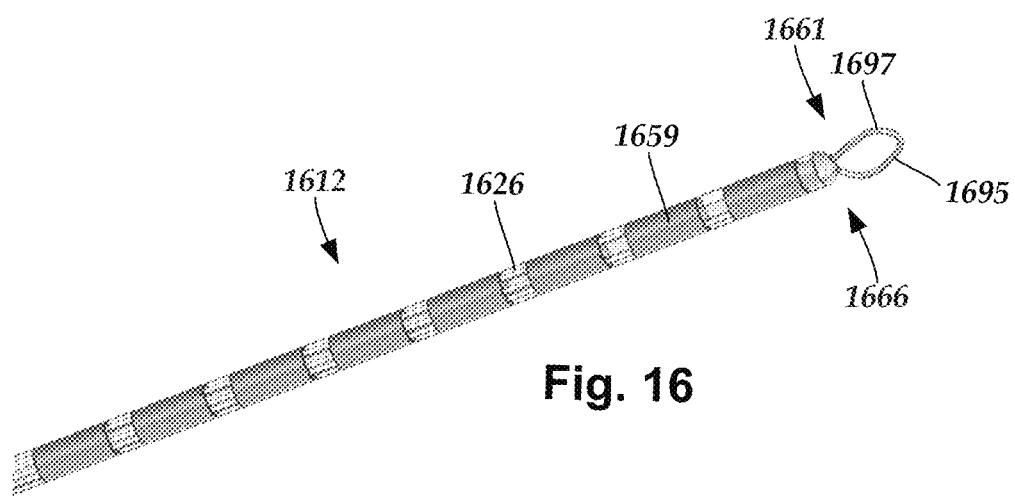
FIG. 16 is a schematic perspective view of another embodiment of a suture-receiving element partially disposed within a body of an electrical stimulation lead, the suture-receiving element including a loop formed from suture and extending outwardly from the lead, according to the invention.

Turning to FIGS. 14-16, in at least some embodiments the suture-receiving elements are partially disposed in the body of the electrical stimulation lead and include one or more loops that extend outwardly therefrom. In at least some embodiments, the one or more loops extend outwardly directly from the body of the electrical stimulation lead. In at least some embodiments, the suture-receiving elements are partially reflowed into the body of the electrical stimulation lead. The loop(s) can be formed from elongated material (e.g., thread, cable, fiber, suture, cord, strand, wire, or the like) suitable for being bent into a loop.

In at least some embodiments, the one or more loops are of sufficient strength for being used to pull an electrical stimulation lead along at least a portion of the tunnel. In at least some embodiments, the one or more loops are of sufficient strength for being used to anchor an electrical stimulation lead to patient tissue. In at least some embodiments, the one or more loops enable or facilitate tissue ingrowth to increase the ability of the loop(s) to anchor the lead to patient tissue. The loop(s) can be rigid, flexible, or include both rigid and flexible portions.

In at least some embodiments, the suture-receiving elements are used in conjunction with one or more of orbital or occipital nerve stimulation. In at least some embodiments, the looped suture-receiving elements are used in conjunction with one or more devices associated with treatment of one or more of treatment of migraines, cluster headaches, and neuralgia.

FIG. 14 shows, in schematic side view, one embodiment of a suture-receiving element 1461 suitable for partially disposing (e.g., reflowing) into the body of an electrical stimulation lead. The suture-receiving element 1461 includes an elongated material 1495 of sufficient strength for pulling an electrical stimulation lead along at least a portion of a tunnel formed from patient tissue or to anchor an electrical stimulation lead to patient tissue, or both. In FIG. 14, the elongated material 1495 is shown as a wire bent back upon itself so that ends 1498 of the wire are in proximity with one another. In at least some embodiments, the wire is rigid. In at least some embodiments, the wire does not cross itself. In at least some embodiments, the wire is bent back on itself to form a U-shape or teardrop-shape.

A collar 1499 is disposed over a portion of the wire so that a bent portion of the wire extends from one end of the collar 1499 while the ends 1498 of the wire extend from an opposing end of the collar 1499. A loop 1497 is formed from the bent portion of the wire extending from the collar 1499. In at least some embodiments, the collar 1499 prevents the ends 1498 of the wire from separating from one another. In at least some embodiments, the collar 1499 maintains integrity of the loop during manufacturing.

FIG. 15 shows, in schematic perspective view, one embodiment of a portion of an electrical stimulation lead 1512 and the suture-receiving element 1461 disposed along a distal portion of the lead 1512. The electrical stimulation lead 1512 includes a body 1559 and electrodes, such as electrode 1526, disposed along the body 1559. The suture-receiving element 1561 is positioned along the lead in a location suitable for enabling the suture-receiving element to receive a suture (e.g., for pulling the attached lead, for anchoring the attached lead, or both). In FIG. 15, the suture-receiving element is shown disposed along a distal tip 1566 of the lead 1512 (e.g., distal to the electrodes 1526).

The loop 1497 includes a largest lateral dimension 1594. In at least some embodiments, the largest lateral dimension 1594 of the loop 1497 is no greater than a transverse diameter 1592 of the lead. Accordingly, in at least some embodiments the one or more loops do not increase the lateral footprint of the lead during use. Consequently, the loop enables or facilitates advancing the lead along portions of the patient that may not be reachable using conventional lead introducers, or anchoring the lead along portions of the patient that may not be anchorable using conventional lead anchors, due to size constraints including, for example, superficial regions of the patient (e.g., in proximity to orbital or occipital nerves).

In the illustrated embodiment, the suture-receiving element 1461 is partially disposed within the body 1559 of the lead while a portion of the loop 1497 is external to the body 1559 of the lead 1512 and extends distally therefrom. In at least some embodiments, the ends 1498 of the wire are disposed in the body 1559 of the lead. In at least some embodiments, at least a portion of the collar 1499 is disposed within the body 1559 of the lead. In FIG. 15, the collar 1499 of the suture-receiving element 1461 is completely disposed within the body 1559 of the lead. In at least some embodiments, the portion of the suture-receiving element disposed in the lead body 1559 is reflowed into lead body 1559. In at least some embodiments, the entire loop is disposed external to the lead. In other embodiments, at least a portion of the loop is formed from the lead body, or the collar, or both.

FIG. 16 shows, in schematic perspective view, another embodiment of a suture-receiving element 1661 disposed along a distal portion of an electrical stimulation lead 1612. The electrical stimulation lead 1612 includes a body 1659 and electrodes, such as electrode 1626, disposed along the body 1659. The lead suture-receiving element 1661 is configured to receive a suture (e.g., for pulling the attached lead, for anchoring the attached lead, or both). In at least some embodiments, the suture-receiving element is disposed along a distal tip 1666 of the lead 1612 (e.g., distal to the electrodes 1626).

The suture-receiving element 1661 includes a loop 1697 formed from an elongated material 1695. The suture-receiving element 1661 is similar to the suture-receiving element 1561 described above in FIGS. 14-15. The loop 1697 of the suture-receiving element 1661, however, is formed from a flexible material. In FIG. 16, the elongated material 1695 is shown as being formed from suture material. One advantage of forming a flexible loop is that, when pulling the lead via the loop, the largest lateral dimension (e.g., 1494 in FIG. 15) of the loop can, in at least some embodiments, be reduced to a length that is no greater than a transverse diameter (e.g., 1592 in FIG. 15) of the lead. Accordingly, in at least some embodiments the loop enables or facilitates advancing the lead along portions of the patient that may not be reachable using conventional lead introducers, or anchoring the lead along portions of the patient that may not be anchorable using conventional lead anchors, due to size constraints including, for example, superficial regions of the patient (e.g., in proximity to orbital or occipital nerves).

In at least some embodiments, the lead suture-receiving element includes at least one radiopaque portion. For example, in embodiments with a loop, the loop (or the collar, or both) is radiopaque. It may be advantageous for the lead suture-receiving element to include at least one radiopaque portion to enable medical imaging, such as fluoroscopy, to be used as a technique to view the positioning of the lead suture-receiving element within the patient. Locating the lead suture-receiving element within the patient may be especially useful as part of a minimally-invasive technique for guiding and/or anchoring the lead at a target stimulation location. Note that, including a radiopaque portion in a suture-receiving element may be equally applicable for along a tunneling tool or a lead blank in addition to, or in lieu of, along either end of an electrical stimulation lead.

In at least some embodiments, the lead suture-receiving element is configured and arranged to disengage from an attached suture or from the lead when an external force applied to the suture-receiving element meets or exceeds a determined threshold. For example, in embodiments with a loop, when the loop is attached to a suture, the loop may break or disengage from the lead (or both) when a potentially dangerous amount of force is applied to the suture to pull the lead. Such a feature may be implemented as a safety concern for limiting the potential for tissue damage while pulling a lead along patient tissue. Moreover, during explantation of the lead such a feature may enable the lead to be removed by application of a force sufficient to disengage the sutures without needing to cut the sutures to remove the lead. Note that, including a safety disengagement system in a suture-receiving element may be equally applicable for along a tunneling tool or a lead blank in addition to, or in lieu of, along either end of an electrical stimulation lead.

FIGS. 5A-5D are schematic perspective views of one embodiment of a lead implantation procedure that includes using the tunneling tool 241 to form a tunnel along patient tissue and to extend the suture 253 therethrough. The suture is then used to pull an electrical stimulation lead, such as any of the leads described herein, through at least a portion of the tunnel. In FIGS. 5A-5D, the lead is shown being implanted along a temple and forehead of a patient.

Figure 5A:
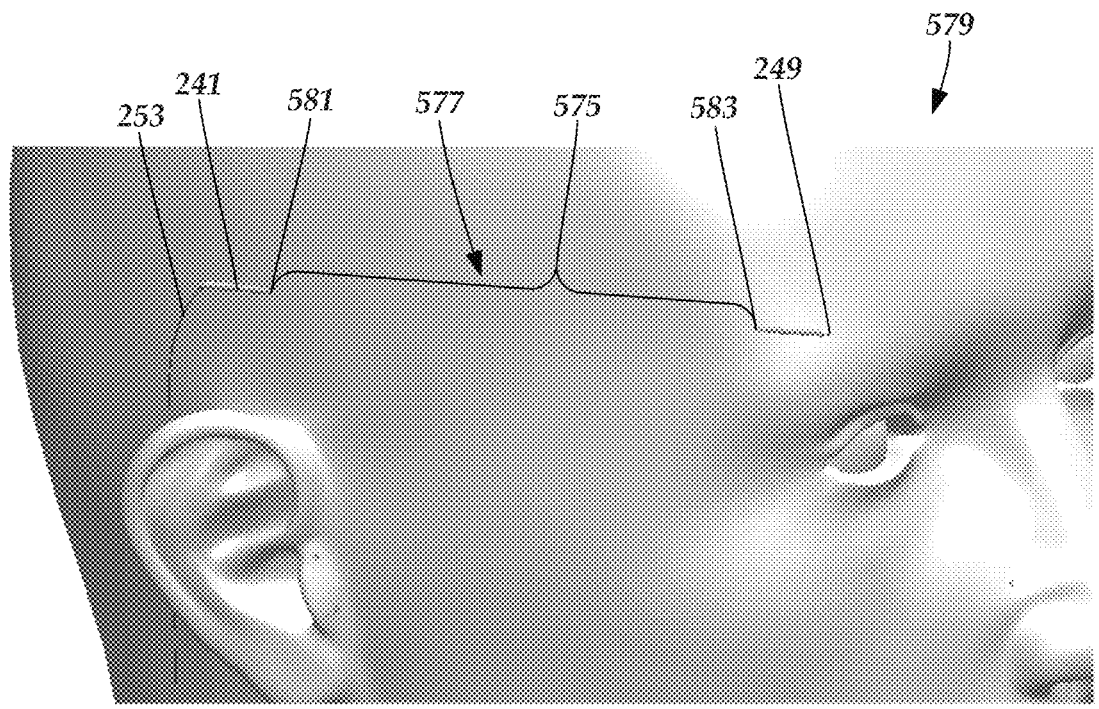
FIGS. 5A-5D are schematic perspective views of one embodiment of a lead implantation procedure that includes using the tunneling tool of FIG. 2A to form a tunnel along patient tissue and to extend a suture along the tunnel that, in turn, is used to pull an electrical stimulation lead at least partway through the tunnel, according to the invention.

FIG. 5A shows the tunneling tool 241 extended through a first leg 575 of a multi-leg tunnel. The first leg 575 extends along the right temple 577 of a patient 579. The first leg 575 of the tunnel extends from an entry location 581 above the patient's right ear and extends to an intermediate waypoint 583 where the blunt tip 249 has exited the patient. The suture 253 is attached to the proximal end of the tunneling tool 241.

In some implantation procedures, such as the illustrated implantation procedure, the tunnel includes at least one bend. In the illustrated embodiment, a bend occurs over the patient's right eye. In some embodiments, the tunneling tool can be bent by a medical practitioner to curve around the bend. In some instances, the bend is too sharp to be navigated around by bending the tunneling tool. In which case, the bend can be tunneled through by dividing the tunnel into several legs, where a first leg ends at an intermediate waypoint positioned along the bend, and a second leg begins at the same intermediate waypoint and proceeds to either another intermediate waypoint or to an egress location.

Once the blunt tip of the tunneling tool reaches the intermediate waypoint and exits the patient, the tunneling tool can be pulled entirely through the intermediate waypoint 583 so as to extend the suture 253 through the entire first leg 575. The tunneling tool 241 can then be reinserted into the intermediate waypoint with a new trajectory, thereby navigating around the anatomical contour. In the illustrated embodiment, the tunneling tool 241 is reinserted into the intermediate waypoint with a trajectory that extends towards an egress location.

Figure 5B:
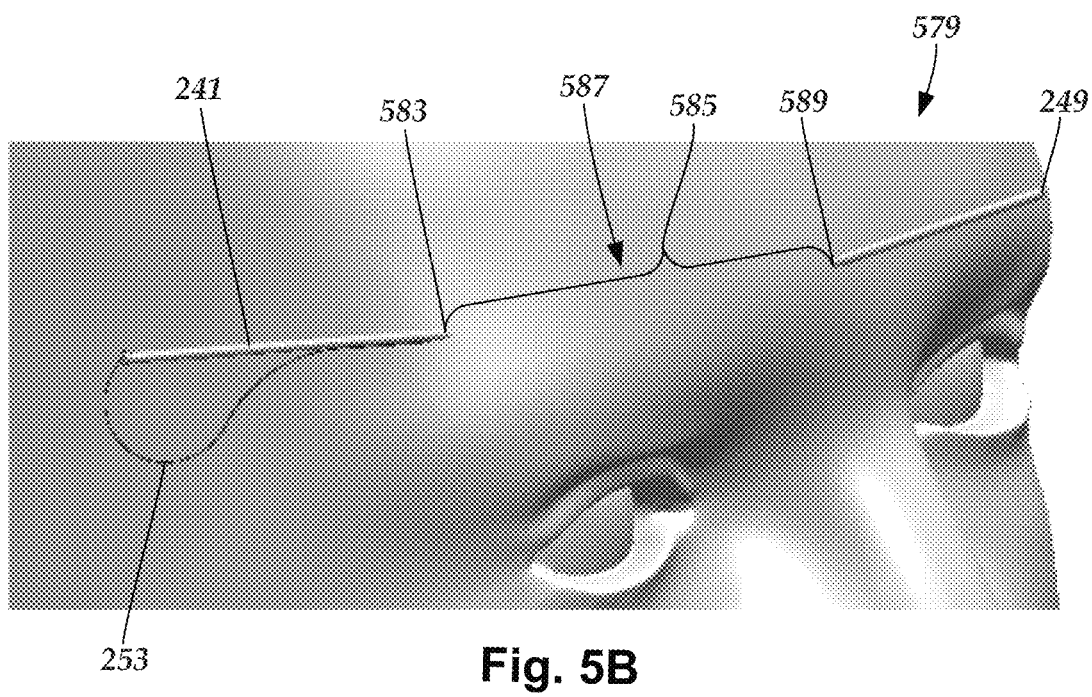

FIG. 5B shows the tunneling tool 241 reintroduced into the patient 559 at the intermediate waypoint 583 and extended through a second leg 585 of the tunnel across the patient's forehead 587 to an egress location 589, from which the blunt tip 249 of the tunneling tool 241 outwardly extends. The suture 253 is still tied to the distal end of the tunneling tool 241 and is extended through the first leg 575 of the tunnel.

Figure 5C:
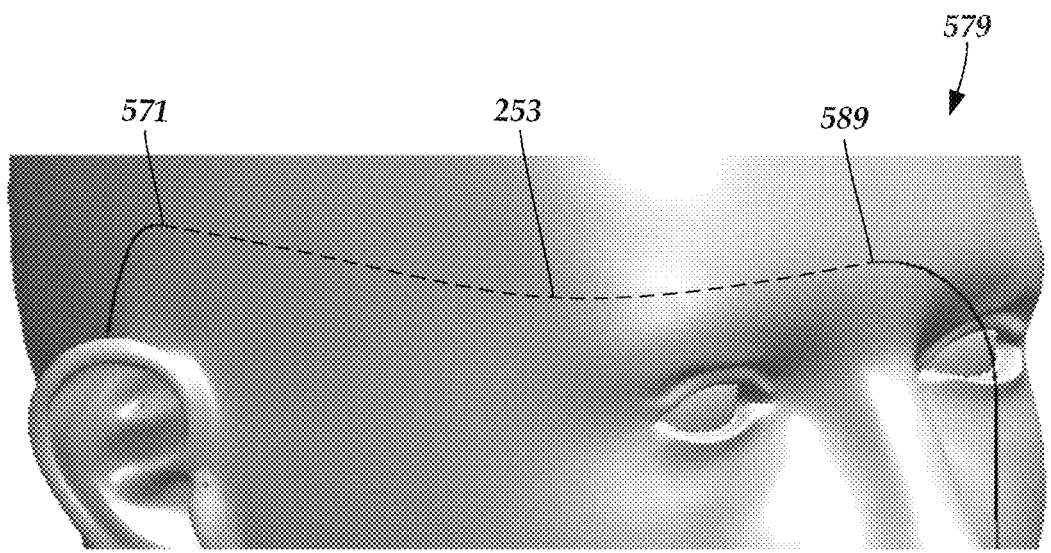

Once the tunneling tool is completely extended through the second leg, the suture extends along the entire tunnel, from the entry location to the egress location. FIG. 5C shows the suture 253 extending along the entire tunnel, from the entry location 581 to the egress location 589. Portions of the suture 253 extend from at least one of the entry location 581 or the egress location 589 to enable the suture 253 to be used to pull a lead (and, optionally, a lead blank) through at least a portion of the tunnel from either (or both) the entry location 581 or the egress location 589.

The blunt tip 249 is configured to create a tunnel through patient tissue, thereby enabling the tunneling tool to advance along the tunnel. In at least some embodiments, the tunneling tool is insufficient to pierce or core patient skin. In at least some embodiments, the bluntness of the blunt tip 249 renders the tunneling tool insufficient to pierce patient skin. In at least some embodiments, an instrument with a sharpened tip (not shown) is used to form at least one of the entry location 581, egress location 589, or intermediate waypoint 583. Note that, in at least some implantation procedures, multiple intermediate waypoints may be utilized, as needed.

Figure 5D:
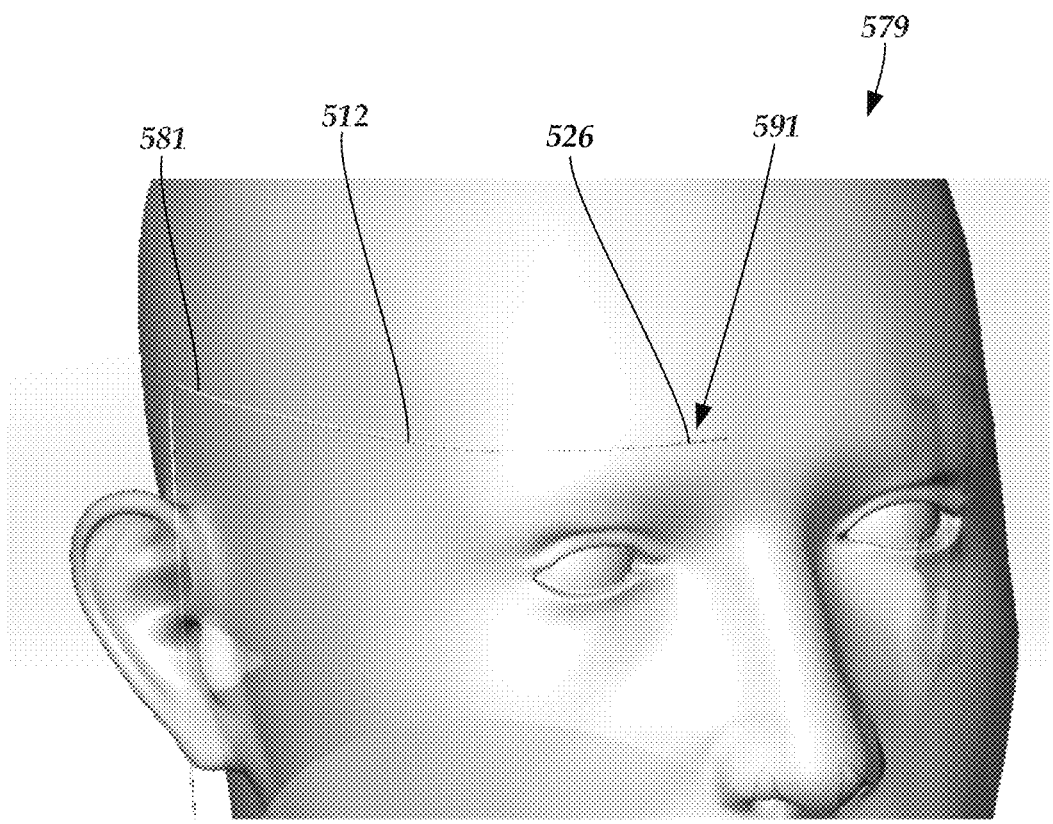

Turning to FIG. 5D, once the tunnel is formed and the suture is extended through the tunnel, a lead can be inserted into the tunnel. The lead can be inserted into the tunnel from either the entry location or the egress location. In at least some embodiments, the tunnel passes through, or in proximity to, a target stimulation location within the patient tissue. In which case, the lead can be positioned along the tunnel so that the electrodes of the lead are positioned at, or in proximity to the target stimulation location.

FIG. 5D shows a lead 512 extended along the tunnel with electrodes of the lead, such as electrode 526, disposed in proximity to a target stimulation location 591. The proximal end of the lead can subsequently be coupled to an IPG (see e.g., 14 of FIG. 1) or an ETS (see e.g., 20 of FIG. 1). The lead is pulled into position using the suture. In some embodiments, the suture is attached to the lead prior to the formation of the tunnel. In other embodiments, the suture is attached to the lead after the tunnel is formed.

Figure 6A:
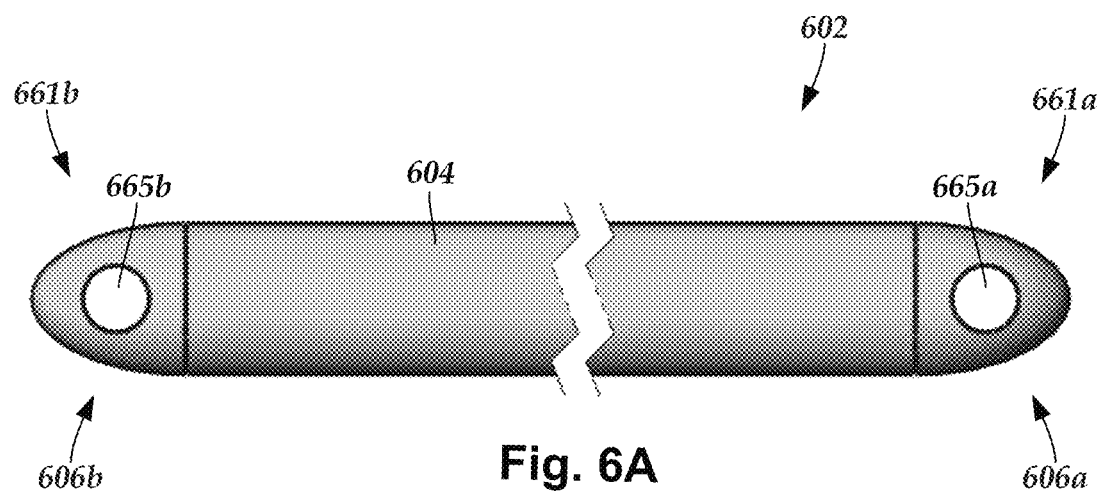
FIG. 6A is a schematic side view of one embodiment of a lead blank with suture-receiving elements positioned along opposing ends of the lead blank, the lead blank suitable for expanding a tunnel formed by the tunneling tool of FIG. 2A along at least one lateral dimension, according to the invention.

Turning to FIG. 6A, in at least some embodiments it may be desirable to expand the tunnel along at least one lateral dimension prior to inserting the lead into the tunnel. In at least some embodiments, a lead blank is used to expand the tunnel along at least one lateral dimension. In at least some embodiments, the lead blank is extended along all, or one or more portions, of the tunnel by pulling the lead blank along the tunnel using the suture. In at least some embodiments, the lead blank includes a suture-receiving element along opposing ends of the lead blank. A first suture-receiving element (disposed along a first end of the lead blank) can be used with the suture extended along the tunnel by the tunneling tool to pull the lead blank along at least a portion of the tunnel, while a second suture (disposed along a second end of the lead blank) can be used to extend one or more sutures along the tunnel for use pulling the lead through the tunnel.

Figure 6B:
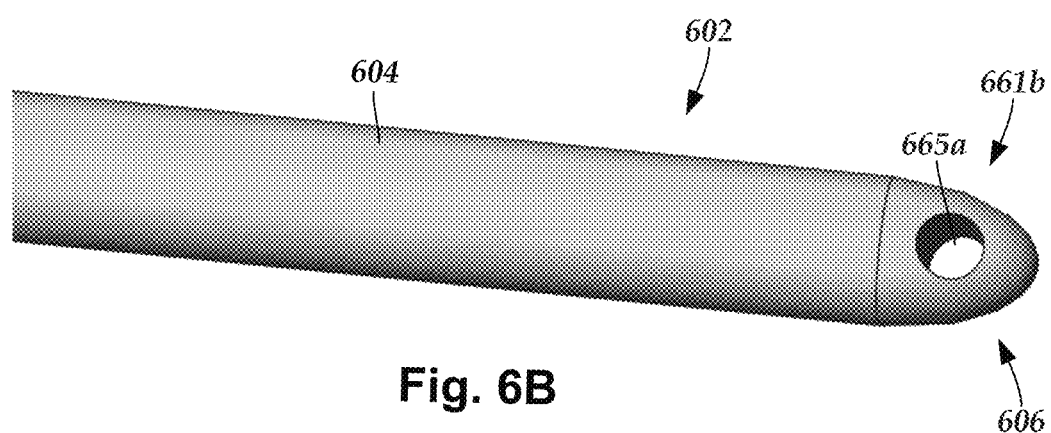
FIG. 6B is a schematic perspective view of a portion of one embodiment of the lead blank of FIG. 6A, according to the invention.

FIG. 6A shows, in schematic side view, one embodiment of a lead blank 602. FIG. 6B shows a portion of the lead blank 602 in perspective view. The lead blank 602 includes a body 604 having blunt tips 606a, 606b along opposing ends of the body 604. Lead-blank suture-receiving elements 661a, 661b are disposed along the blunt tips 606a, 606b, respectively. In at least some embodiments, the lead-blank suture-receiving elements 661a, 661b define eyelets 665a, 665b, respectively. In alternate embodiments, the body 604 includes a single blunt tip. In alternate embodiments, the body 604 includes a single eyelet.

In the embodiment illustrated in FIGS. 6A-6B, the body 604 of the lead blank 602 is shown having a round transverse profile. Additionally, in the illustrated embodiment, the entire body 604 between the blunt tips 606a, 606b has an isodiametric transverse dimension. Accordingly, when the lead blank 602 is pulled through a tunnel formed by a tunneling tool with a largest transverse dimension that is smaller than the diameter of the body 604 of the lead blank 602 between the blunt tips 606a, 606b, the lead blank can be used to expand the tunnel along all lateral dimensions. The lead blank 602 may be especially useful for expanding the tunnel to accommodate a percutaneous lead, where the lead body may have an isodiametric transverse profile proximal to the distal tip.

Figure 7A:
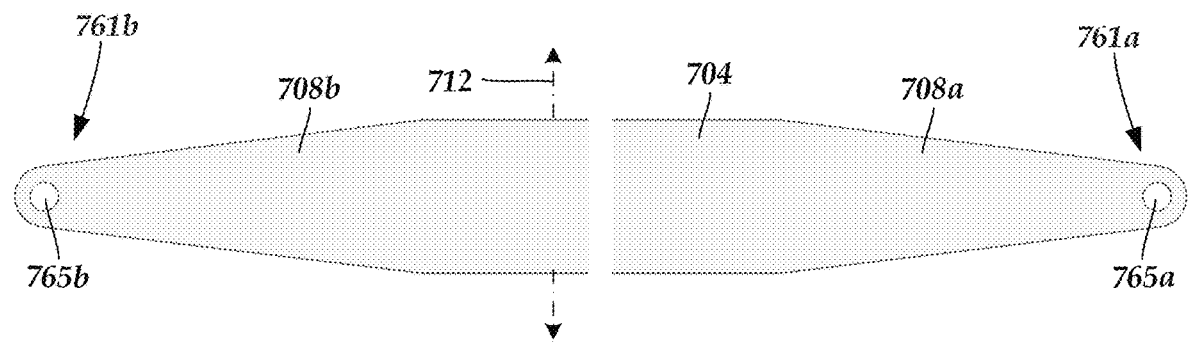
FIG. 7A is a schematic side view of another embodiment of a lead blank with suture-receiving elements positioned along opposing ends of the lead blank, the lead blank suitable for expanding a tunnel formed by the tunneling tool of FIG. 2A along at least one lateral dimension, according to the invention.
Figure 7B:
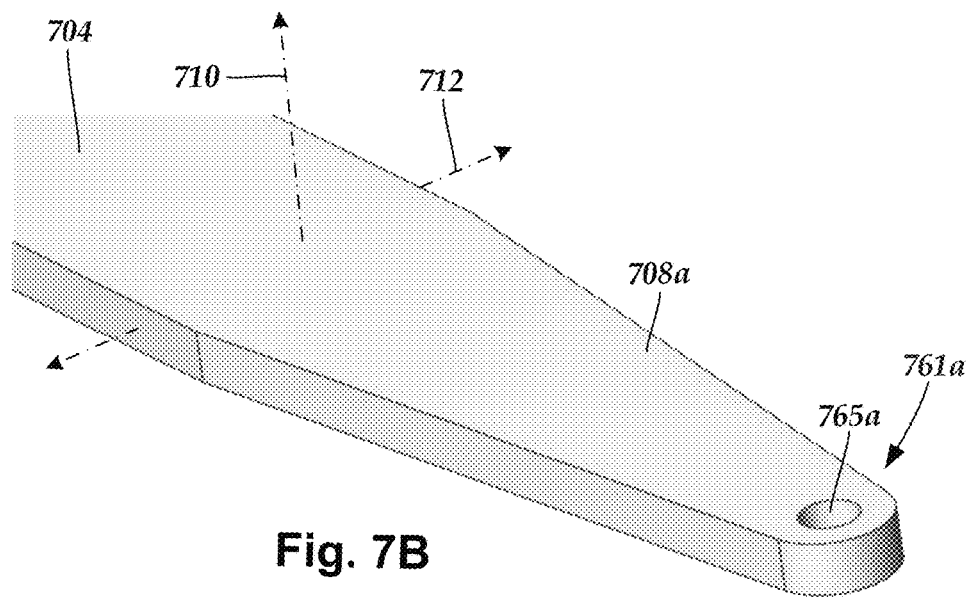
FIG. 7B is a schematic perspective view of a portion of one embodiment of the lead blank of FIG. 7A, according to the invention.

FIG. 7A shows, in schematic side view, another embodiment of a lead blank 702. FIG. 7B shows a portion of the lead blank 702 in perspective view. The lead blank 702 includes an intermediate section 704 disposed between two blunt necks 708a, 708b. Lead-blank suture-receiving elements 761a, 761b are disposed along tips 706a, 706b of the blunt necks 708a, 708b, respectively. In at least some embodiments, the lead-blank suture-receiving elements 761a, 761b define eyelets 765a, 765b, respectively, suitable for receiving sutures.

In the embodiment illustrated in FIGS. 7A-7B, the intermediate section 704 of the lead blank 702 is shown having a rectangular transverse profile with a first dimension 710 and a second dimension 712 perpendicular to the first dimension 710. The second dimension 712 is larger than the first dimension 710. In at least some embodiments, second dimension 712 is significantly larger than the first dimension 710. The second dimension 712 of the intermediate section 704 of the lead blank 702 forms the largest lateral dimension of the lead blank 704.

Additionally, in the illustrated embodiment, the entire intermediate section 704 between the blunt necks 708a, 708b has constant lateral dimensions. Accordingly, when the lead blank 702 is pulled through a tunnel formed by a tunneling tool with a largest lateral dimension that is smaller than the second dimension 712 of the intermediate section 704 of the lead blank 702, the lead blank can be used to expand the tunnel mostly, or exclusively, along a single lateral dimension. The lead blank 702 may be especially useful for expanding the tunnel to accommodate a paddle lead, where the paddle body (1006 of FIG. 10) typically has a rectangular-shaped transverse profile.

Figure 8:
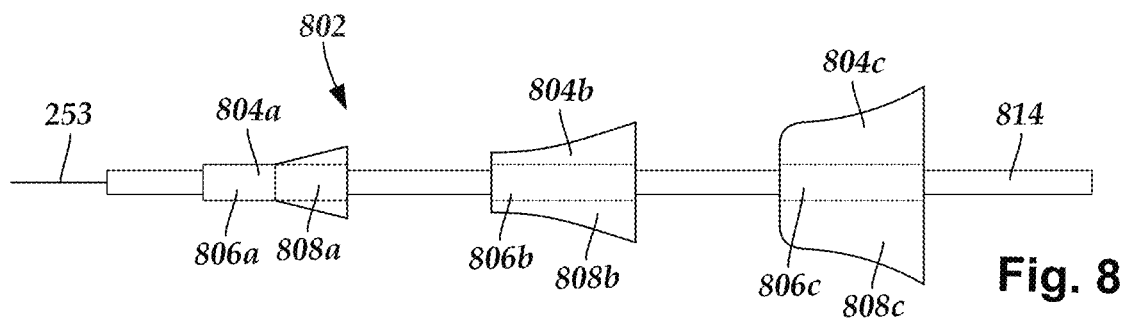
FIG. 8 is a schematic side view of yet another embodiment of a lead blank suitable for expanding a tunnel formed by the tunneling tool of FIG. 2A along at least one lateral dimension, the lead blank including multiple pieces arranged in order of ascending transverse dimension, according to the invention.

Turning to FIG. 8, the previous embodiments of lead blanks, as shown in FIGS. 6A-7B, are single-piece devices. In alternate embodiments, the lead blank is formed from multiple pieces arranged in order of increasing lateral dimensions. It may be an advantage to use a lead blank formed from multiple pieces to enable each individual piece to have a shorter length than were a single-piece lead blank to be used to expand a tunnel by the same amount. A shorter length may increase the turning radius of the lead blank along the tunnel, thereby potentially enabling the lead blank to better conform to anatomical contours.

FIG. 8 shows, in schematic side view, yet another embodiment of a lead blank 802 with multiple pieces 804a, 804b, and 804c longitudinally-offset from one another, arranged in order of ascending length along at least one lateral dimension. In at least some embodiments, the lead blank 802 has a round transverse profile. In other embodiments, the lead blank 802 has an oblong, or polygonal (regular or irregular) transverse profile.

The individual pieces 804a, 804b, 804c of the lead blank 802 each include a body 806a, 806b, 806c, respectively. The individual pieces 804a, 804b, 804c are coupled together by a connector 814. The individual pieces 804a, 804b, 804c of the lead blank 802 each include a connector-receiving element 808a, 808b, 808c, respectively, for coupling the body to the connector. In some embodiments, at least one of the individual pieces 804a, 804b, 804c of the lead blank 802 is configured to slide along the connector 814 relative to the other individual pieces 804a, 804b, 804c. In other embodiments, the individual pieces 804a, 804b, 804c of the lead blank 802 are longitudinally-spaced-apart from one another by a constant distance. In at least some embodiments, at least one of the individual pieces 804a, 804b, 804c of the lead blank 802 is configured to rotate about the connector 814 relative to at least one other of the individual pieces 804a, 804b, 804c. In other embodiments, each of the individual pieces 804a, 804b, 804c of the lead blank 802 is rotationally fixed relative to the other pieces. In at least some embodiment, the connector 814 functions as a lead-blank suture-receiving element. In other some embodiments, a lead-blank suture-receiving element is disposed along at least one of the individual pieces 804a, 804b, 804c of the lead blank 802.

Figure 9A:
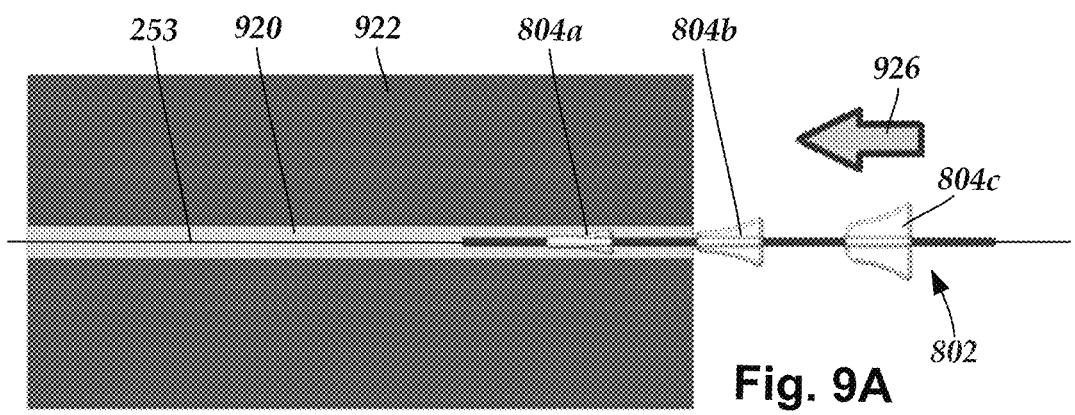
FIGS. 9A-9C are schematic side views of one embodiment of the lead blank of FIG. 8 being used to expand a tunnel formed by the tunneling tool of FIG. 2A along at least one lateral dimension, according to the invention.
Figure 9B:
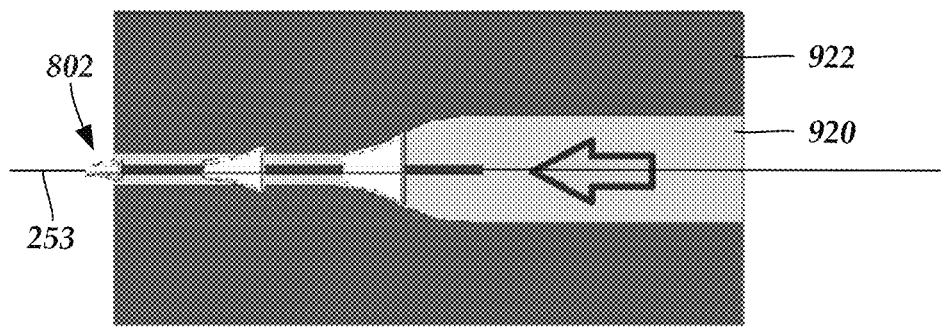
Figure 9C:
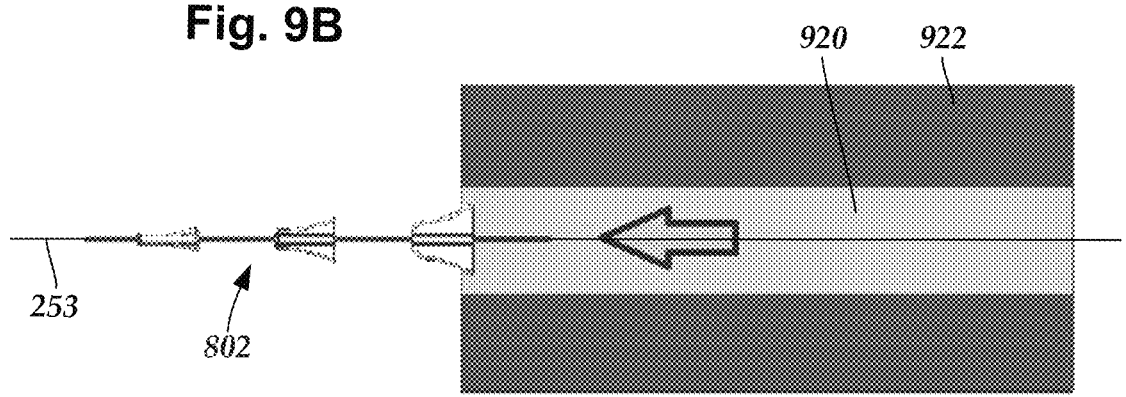

FIGS. 9A-9C show, in schematic side view, one embodiment of the lead blank 802 being used to expand a tunnel 920 extending through patient tissue 922. In the embodiment shown in FIGS. 9A-9C, the lead blank 802 has a round transverse profile. Accordingly, when the lead blank 802 is extended through the tunnel 920, and the tunnel 920 does not have any lateral dimensions that are larger than the transverse profile of the lead blank 802, the tunnel 920 is expanded to have a round transverse profile. Such a shape may be especially useful for receiving a percutaneous lead.

FIG. 9A shows the lead blank 802 partially inserted into the tunnel 920. The lead blank 802 can be inserted into the tunnel from either an entry location or an egress location. The lead blank 802 is oriented so that the individual pieces 804a, 804b, 804c of the lead blank 802 enter the tunnel 920 from smallest lateral dimensions to largest lateral dimensions. In FIG. 9A, the lead blank 802 is shown entering the tunnel 920 in the direction shown by directional arrow 926, with the piece 804a entering first, followed by the piece 804b, then the piece 804c.

FIG. 9B shows the lead blank 802 fully inserted into, and partially extended along, the tunnel 920. As shown in FIG. 9B, the portion of the tunnel 920 through which the lead blank 802 has already passed has at least some larger lateral dimensions than the portion of the tunnel 920 through which the lead blank 802 has not yet passed.

FIG. 9C shows the lead blank 802 exiting a far end of the tunnel 920 from where the lead blank 802 entered the tunnel 920. As shown in FIG. 9C, the entire length of the tunnel 920 has at least some larger lateral dimensions than the tunnel 920 prior to passage of the lead blank 802 therethrough.

Figure 10:
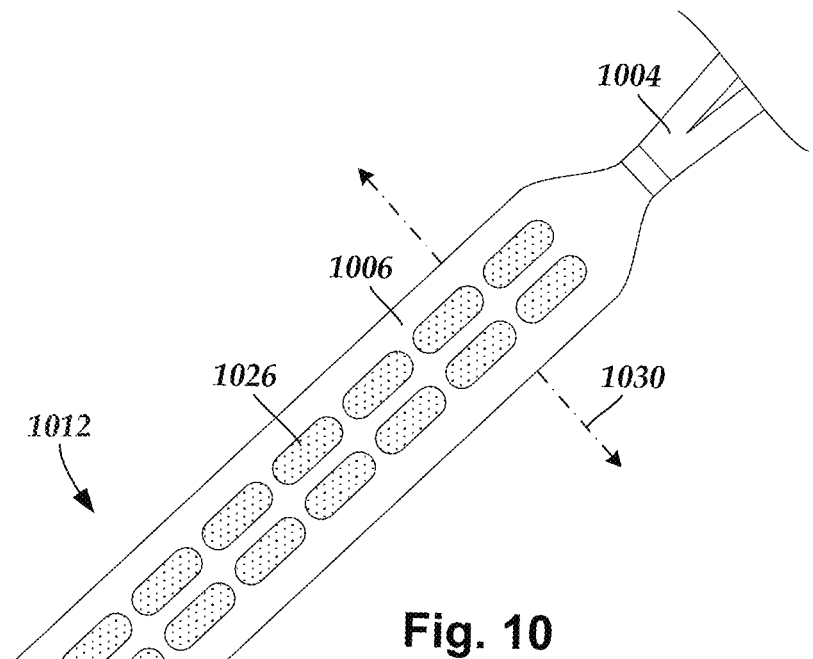
FIG. 10 is a schematic side view of one embodiment of a distal portion of a paddle lead, according to the invention.

In some instances, it is desired to implant a lead that does not have a round transverse profile, or that includes one or more portions with a transverse profile that is not round. FIG. 10 shows, in schematic side view, one embodiment of a distal portion of a paddle lead 1012. The paddle lead 1012 includes a paddle body 1006 disposed along a distal portion of at least one lead body 1004. Electrodes, such as electrode 1026, are disposed along the paddle body 1006 in one or more columns. In FIG. 10, the paddle body 1006 includes two columns of electrodes 1026. In FIG. 10, the paddle body 1006 has a transverse profile that is not round. Instead, the paddle body 1006 has a transverse profile that includes a largest lateral dimension 1030.

Figure 11:
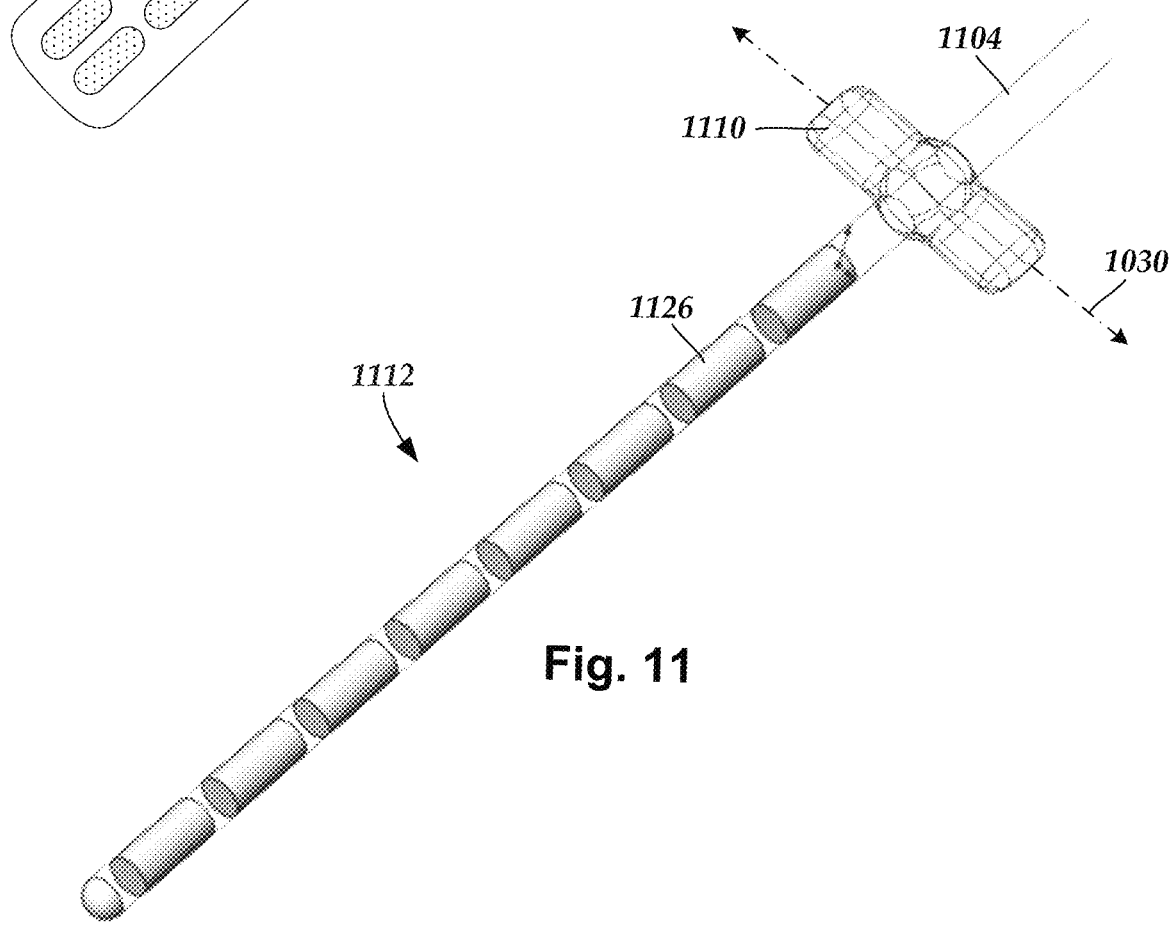
FIG. 11 is a schematic perspective view of one embodiment of an anchoring unit disposed along a distal portion of a percutaneous lead, according to the invention.

FIG. 11 shows, in schematic side view, one embodiment of a distal portion of a percutaneous lead 1112. The percutaneous lead 1112 includes a lead body 1104 having a round transverse profile proximal to a distal tip. Electrodes, such as electrode 1126, are disposed along the distal portion of the lead body 1104. In the illustrated embodiment, an anchoring unit 1110 is disposed along the distal portion of the lead proximal to the electrodes 1126. In FIG. 11, the portion of the lead 1112 along which the anchor 1110 is disposed has a transverse profile that is not round. Instead, the portion of the lead 1112 along which the anchoring unit 1110 is disposed has a transverse profile that includes a largest lateral dimension 1130.

In some instances, it may be beneficial to extend the lead blank only partially through the tunnel, thereby forming a pocket along one end of the tunnel to accommodate a locally-oversized portion of a lead (e.g., a portion of the lead along the longitudinal length with at least one lateral dimension that is larger than all of the lateral dimensions of the lead along other longitudinally-offset portions of the lead). In at least some embodiments, the lead blank is extended along no more than half a length of the tunnel.

In at least some embodiments, the pocket is formed to have perpendicular lateral dimensions of significantly-unequal length, while the remaining portion of the tunnel has a smaller length along at least one lateral dimension. In other embodiments, the pocket is formed to have a round transverse profile, while the remaining portion of the tunnel has a smaller length along at least one lateral dimension.

FIGS. 12A-12D show, in schematic side view, one embodiment of the lead blank 802 being used to expand one end of a tunnel extending through patient tissue to accommodate the paddle lead 1012. Note that the lead blank 802 is shown as an example. The expansion of one end (or both end) of a tunnel can be performed with any of the lead blanks described above. In some embodiments, different lead blanks are extended along opposing ends of the tunnel. In some embodiments, multiple different lead blanks are extended along the same, or overlapping, portions of the tunnel.

Figure 12A:
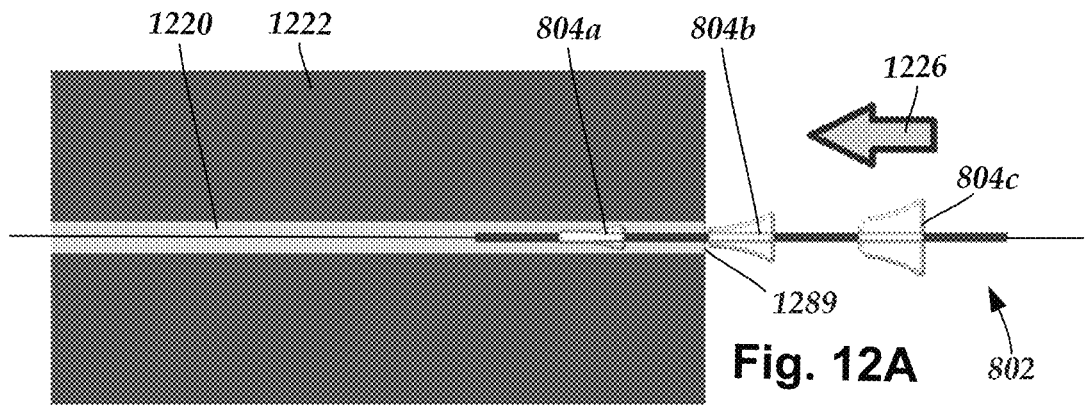
FIGS. 12A-12D are schematic side views of one embodiment of a portion of a lead implantation procedure that includes the lead blank of FIG. 8 being used to expand a tunnel formed by the tunneling tool of FIG. 2A along at least one lateral dimension to accommodate the lead of FIG. 10, according to the invention.

FIG. 12A shows the lead blank 802 partially inserted into the tunnel 1220. The lead blank 802 can be inserted into the tunnel from either an entry location or an egress location. In instances where it is desired to accommodate a lead with a distal portion having an oversized region (e.g., the distal portion of the lead having at least one lateral dimension that is larger than all of the lateral dimensions of the lead along other longitudinally-offset portions of the lead), the lead blank 802 is inserted into the tunnel 1220 from an egress location 1289. The lead blank 802 is oriented so that the individual pieces 804a, 804b, 804c of the lead blank 802 enter the tunnel 1220 from smallest lateral dimensions to largest lateral dimensions. In FIG. 12A, the lead blank 802 is shown entering the tunnel 920 in the direction shown by directional arrow 1226, with the piece 804a entering first, followed by the piece 804b, then the piece 804c.

Figure 12B:
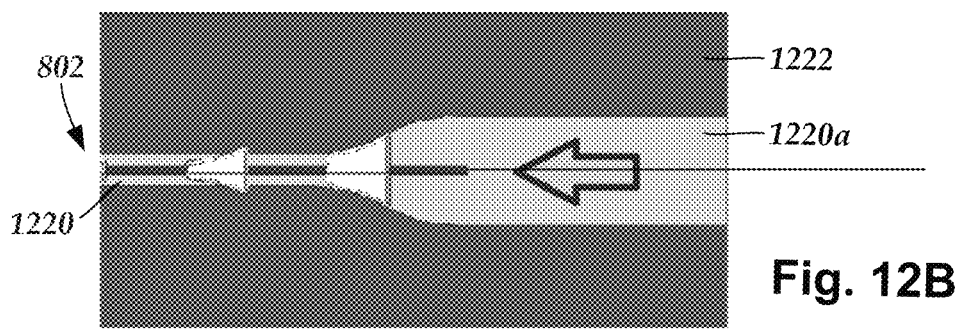

FIG. 12B shows the lead blank 802 fully inserted into, and partially extended along, the tunnel 1220. As shown in FIG. 12B, the portion of the tunnel 1220 through which the lead blank 802 has already passed has formed a pocket 1220a having at least one lateral dimension that is larger than the same dimension along the portion of the tunnel 1220 through which the lead blank 802 has not yet passed.

Figure 12C:
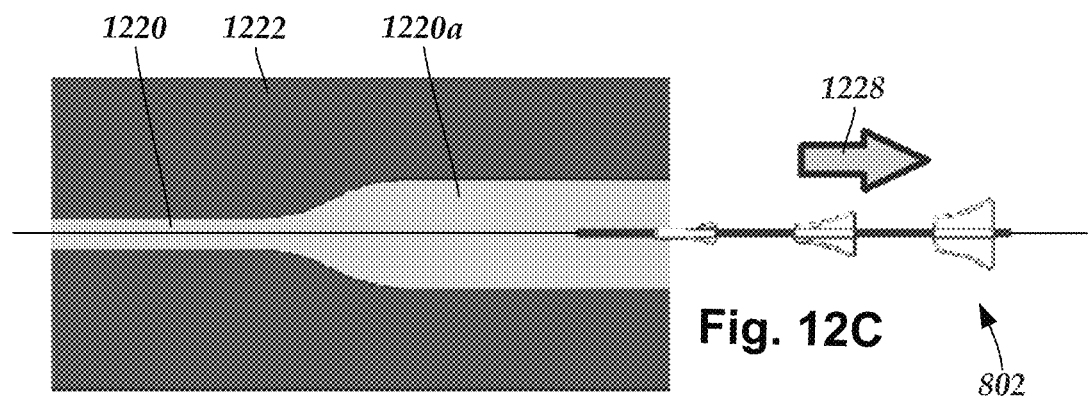

FIG. 12C shows the lead blank 802 being pulled the opposite direction, as indicated by directional arrow 1228, back out of the tunnel 1220 through the egress location 1289. The tunnel 1220 includes a pocket 1220a along a portion of the tunnel 1220 adjacent to the egress location 1289. The pocket 1220a includes at least one lateral dimension large enough to accommodate the largest lateral dimension (1030 in FIG. 10) of the paddle lead 1012.

Figure 12D:
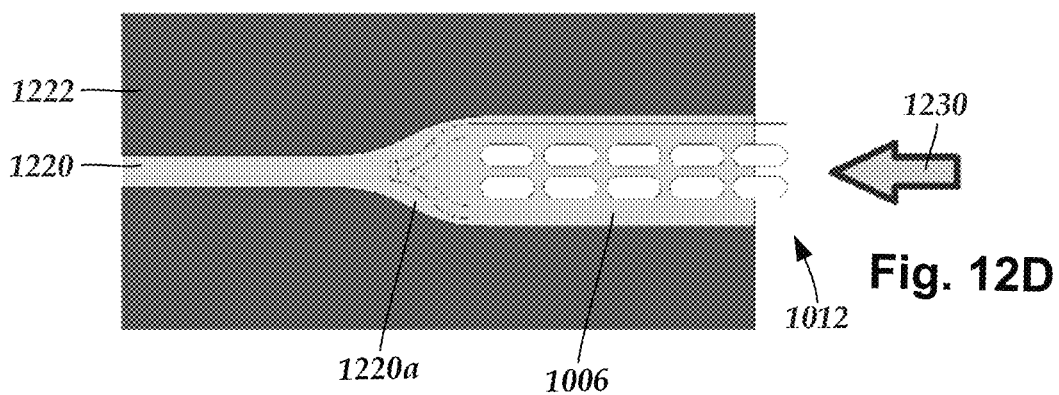

FIG. 12D shows the lead blank 802 removed from the egress location 1289 of the tunnel 1220. The paddle lead 1012 is inserted into the tunnel 1220 with the paddle body 1006 of the lead disposed in the pocket 1220a. Note that the paddle lead 1012 is inserted into the tunnel 1220 from the egress location 1289, in the direction indicated by directional arrow 1230, so as to avoid extending the paddle body 1006 along the portion of the tunnel outside of the pocket 1220a, where the lateral dimensions of the tunnel would not accommodate the paddle body along at least one lateral dimension.

Figure 13A:
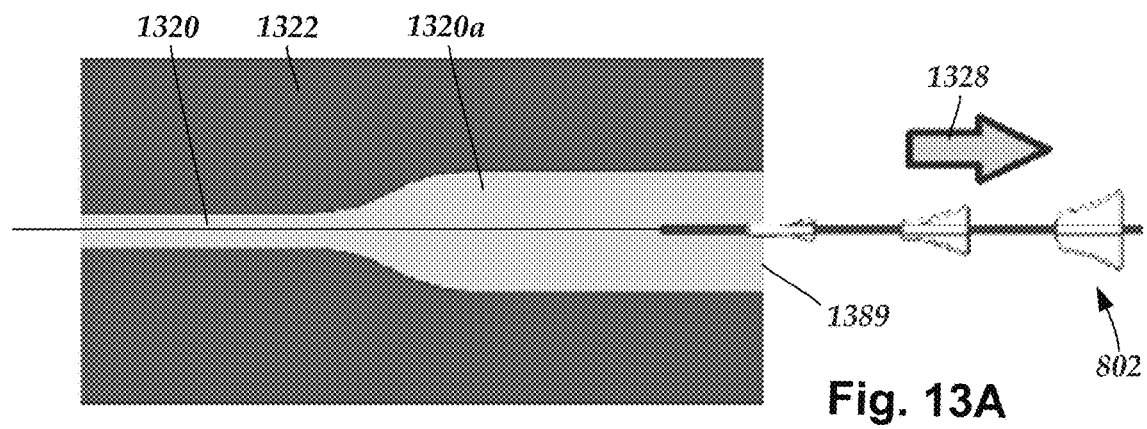
FIGS. 13A-13B are schematic side views of one embodiment of a portion of a lead implantation procedure that includes the lead blank of FIG. 8 being used to expand a tunnel formed by the tunneling tool of FIG. 2A along at least one lateral dimension to accommodate the lead and anchoring unit of FIG. 11, according to the invention.
Figure 13B:
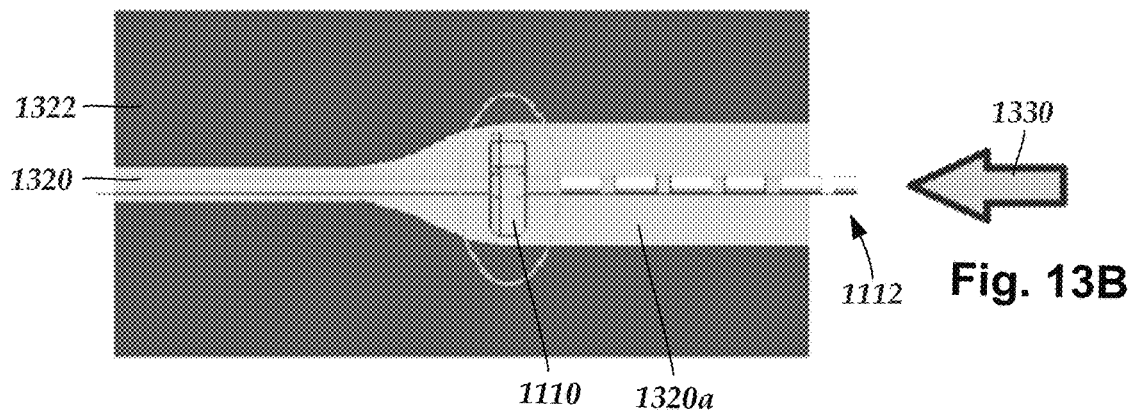

The same pocket-forming technique described above can be used for creating a pocket suitable for receiving the lead 1112. FIGS. 13A-13B show, in schematic side view, one embodiment of the lead blank 802 being used to expand one end of a tunnel extending through patient tissue to accommodate the percutaneous lead 1112. Note that the lead blank 802 is shown as an example. The expansion of one end (or both end) of a tunnel can be performed with any of the lead blanks described above.

FIG. 13A shows the lead blank 802 disposed in a tunnel 1320 formed in patient tissue 1322. The lead blank 802 was inserted into, and partially extended along, the tunnel 1220 from an egress location 1389, similar to what is shown in FIGS. 12A-12B. The portion of the tunnel 1320 through which the lead blank 802 has already passed has formed a pocket 1320a having at least one lateral dimension that is larger than the same dimension along the portion of the tunnel 1320 through which the lead blank 802 has not yet passed.

In FIG. 13A, the lead blank 802 is shown being pulled the opposite direction, as indicated by directional arrow 1328, from the direction it entered the tunnel 1230 so that the lead blank 802 is now heading back out of the tunnel 1320 through the egress location 1389. The tunnel 1320 includes a pocket 1320a along a portion of the tunnel 1320 adjacent to the egress location 1389. The pocket 1320a includes at least one lateral dimension large enough to accommodate the largest lateral dimension (1130 of FIG. 11) of the lead 1112.

FIG. 13B shows the lead blank 802 removed from the egress location 1389 of the tunnel 1320. The lead 1112 is inserted into the tunnel 1320 with the anchoring unit 1110 of the lead 1112 disposed in the pocket 1320a. Note that the paddle lead 1012 is inserted into the tunnel 1220 from the egress location 1289, in the direction indicated by directional arrow 1330, so as to avoid extending the anchoring unit 1110 along the portion of the tunnel outside of the pocket 1320a, where the lateral dimensions of the tunnel would not accommodate the anchoring unit along at least one lateral dimension.

It may be advantageous to form a pocket to accommodate a lead with a local oversized region, as described above with reference to FIGS. 12A-13B, to reduce the amount of collateral patient tissue undesirably carved out during a lead implantation procedure. In addition to reducing the amount of undesired collateral tissue damage, providing a pocket may facilitate anchoring of the lead by preventing proximal lead migration because the locally oversized region of the lead may not be able to undesirably slide through the tunnel proximal to the pocket.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A medical device kit, comprising:
   a tunneling tool configured and arranged to form a tunnel through patient tissue for receiving an electrical stimulation lead, the tunneling tool comprising
      a tunneling-tool body having an elongated shape with a proximal portion and a distal portion, the tunneling-tool body formed from a material configured and arranged to be manually bent prior to insertion into patient tissue to conform to an anatomical contour through which the tunnel is to extend,
      a blunt tip disposed at the distal portion, the blunt tip configured and arranged to tunnel through patient tissue, and
      a tunneling-tool suture-receiving element disposed along the proximal portion of the tunneling-tool body, the tunneling-tool suture-receiving element configured and arranged to receive a suture extendable along the tunnel formed by the tunneling tool; and
   a lead blank configured and arranged to expand a tunnel formed by the tunneling tool along at least one lateral dimension when the lead blank is extended through the tunnel, the lead blank having at least one lateral dimension that is larger than any lateral dimension of the tunneling tool.

2. The medical device kit of claim 1, wherein the blunt tip of the tunneling tool is not sufficient to pierce patient skin.

3. The medical device kit of claim 1, further comprising at least one suture attached to the tunneling-tool suture-receiving element.

4. The medical device kit of claim 1, wherein the lead blank comprises at least one lead-blank suture-receiving element configured and arranged for receiving the suture extended through the tunnel by the tunneling tool and being pulled through the tunnel using the suture.

5. The medical device kit of claim 1, wherein the lead blank is a single-piece structure.

6. The medical device kit of claim 1, wherein the lead blank is a multi-piece structure comprising a first piece and at least one longitudinally-offset second piece coupled, or coupleable, to the first piece, wherein the first piece and the at least one longitudinally-offset second piece are each configured and arranged to expand patient tissue.

7. The medical device kit of claim 6, wherein a largest lateral dimension of the first piece is smaller than a largest lateral dimension of the at least one longitudinally-offset second piece.

8. A medical device system, comprising:
   the medical device kit of claim 1; and
   an electrical stimulation lead configured and arranged for insertion into a tunnel formed by the tunneling tool of the medical device kit, the electrical stimulation lead comprising
      a lead body having a proximal portion and a distal portion,
      a plurality of electrodes disposed along the distal portion of the lead body, and
      a lead suture-receiving element coupled, or coupleable, to the lead body, the lead suture-receiving element configured and arranged to receive a suture extending through the tunnel formed by the tunneling tool and being pulled through the tunnel using the suture.

9. The medical device system of claim 8, wherein the tunneling-tool body has a largest lateral dimension that is no larger than a largest lateral dimension of the lead body.

10. The medical device system of claim 8, wherein at least one of the tunneling-tool suture-receiving element or the lead suture-receiving element is formed as an eyelet.

11. The medical device system of claim 8, wherein the lead suture-receiving element is disposed along the distal portion of the lead body.

12. The medical device system of claim 8, wherein the lead suture-receiving element is disposed along the proximal portion of the lead body.

13. The medical device system of claim 8, the lead blank comprising a first lead blank suture-receiving element and a second lead blank suture-receiving element, the first lead blank suture-receiving element configured and arranged to couple to the tunneling-tool suture-receiving element of the tunneling tool by a first suture, and the second lead blank suture-receiving element configured and arranged to couple to the lead suture-receiving element by a second suture.

14. The medical device system of claim 9, wherein the distal portion of the lead body of the electrical stimulation lead has a distal tip and the lead suture-receiving element of the electrical stimulation lead comprises either a) at least one of an eyelet disposed along a plug coupleable with the distal tip of the lead body or b) elongated material partially disposed in the lead body and forming a loop extending outwardly from the distal tip.

15. A method for implanting an electrical stimulation lead into a patient, the method comprising:
providing the medical device system of claim 9;
extending a suture through a tunnel formed through patient tissue, using the tunneling tool of the medical device system, from an entry location where the tunnel enters patient tissue to an egress location distinct from the entry location where the tunnel exits patient tissue; and
pulling the electrical stimulation lead of the medical device system into the tunnel using the suture.

16. The method of claim 15, wherein extending a suture through a tunnel formed through patient tissue, using the tunneling tool of the medical device system, from an entry location where the tunnel enters patient tissue to an egress location distinct from the entry location where the tunnel exits patient tissue comprises exiting patient tissue at an intermediate waypoint along the tunnel between the entry location and the egress location and re-entering patient tissue at the intermediate waypoint.

17. The method of claim 15, further comprising enlarging at least a portion of the tunnel along at least one lateral dimension by pulling the lead blank through at least a portion of the tunnel from either the entry location or the egress location using the suture, and using the lead blank for pulling the electrical stimulation lead of the medical device system into the tunnel using another suture.

18. The method of claim 15, wherein pulling the lead blank through at least a portion of the tunnel from either the entry location or the egress location comprises pulling the lead blank along less than half of a length of the tunnel in a first direction, and subsequently pulling the lead blank in a second direction that is opposite to the first direction to remove the lead blank from the tunnel, thereby forming a pocket along one end of the tunnel with at least one lateral dimension that is larger than any lateral dimension of remaining portions of the tunnel.

19. A method of anchoring an electrical stimulation lead to patient tissue, the method comprising:
providing the medical device system of claim 14;
advancing the electrical stimulation lead to a target location within a patient; and
attaching the lead suture-receiving element of the electrical stimulation lead to patient tissue, via the suture, to anchor the electrical stimulation lead in proximity to the target location.

* * * * *